United States Patent [19]
Lenk et al.

[11] Patent Number: 5,830,498
[45] Date of Patent: *Nov. 3, 1998

[54] LIPOSOMAL-POLYENE PRELIPOSOMAL POWDER AND METHOD FOR ITS PREPARATION

[75] Inventors: Robert P. Lenk, New Waverly; Reeta Mehta; Gabriel Lopez-Berestein, both of Houston, all of Tex.

[73] Assignees: Board of Regents, The University of Texas System, Austin; Aronex Pharmaceuticals, Inc., The Woodlands, both of Tex.

[*] Notice: The term of this patent shall not extend beyond the expiration date of Pat. No. 5,178,875.

[21] Appl. No.: 535,885

[22] Filed: Sep. 28, 1995

Related U.S. Application Data

[63] Continuation of Ser. No. 204,642, Mar. 1, 1994, abandoned, which is a continuation of Ser. No. 902,891, Jun. 23, 1992, abandoned, which is a continuation of Ser. No. 640,707, Jan. 14, 1991, Pat. No. 5,178,875, which is a continuation-in-part of Ser. No. 588,143, Sep. 25, 1990, abandoned, which is a division of Ser. No. 152,183, Feb. 4, 1988, abandoned, which is a continuation-in-part of Ser. No. 109,813, Oct. 16, 1987, Pat. No. 4,950,432.

[51] Int. Cl.$^6$ .................................................. A61K 9/127
[52] U.S. Cl. .............................. 424/450; 264/4.1; 264/4.3
[58] Field of Search .............................. 424/450; 264/4.1, 264/4.3

[56] References Cited

U.S. PATENT DOCUMENTS

| | | |
|---|---|---|
| 4,229,360 | 10/1980 | Schneider et al. . |
| 4,247,411 | 1/1981 | Vanlerberghe . |
| 4,311,712 | 1/1982 | Evans . |
| 4,370,349 | 1/1983 | Evans . |
| 4,673,567 | 6/1987 | Jizomoto . |
| 4,687,762 | 8/1987 | Fukushima et al. . |
| 4,744,989 | 5/1988 | Payne et al. . |
| 4,762,720 | 8/1988 | Jizomoto . |
| 4,766,046 | 8/1988 | Abra . |
| 4,812,312 | 3/1989 | Lopez-Berestein . |
| 4,830,858 | 5/1989 | Payne et al. . |
| 4,880,635 | 11/1989 | Janoff et al. . |
| 4,883,665 | 11/1989 | Miyazima et al. . |
| 4,897,355 | 1/1990 | Eppstein et al. . |
| 4,935,171 | 6/1990 | Bracken . |
| 4,950,432 | 8/1990 | Mehta et al. . |
| 4,963,362 | 10/1990 | Rahman et al. . |
| 4,971,802 | 11/1990 | Tarcsay . |
| 4,994,213 | 2/1991 | Aitcheson et al. . |
| 4,999,199 | 3/1991 | Anaissie . |
| 5,178,875 | 1/1993 | Lenk et al. . |

FOREIGN PATENT DOCUMENTS

| | | |
|---|---|---|
| 0152379 | 8/1985 | European Pat. Off. . |
| 0158441 | 10/1985 | European Pat. Off. . |
| 0282405 | 9/1988 | European Pat. Off. . |
| WO 89/03208 | 4/1989 | WIPO . |
| WO 89/11850 | 12/1989 | WIPO . |

OTHER PUBLICATIONS

Iqbal et al., "Pre-Resonance Raman Spectra and Conformations of Nystatin in Powder, Solution and Phospholipid-Cholesterol Multilayers," Biochimica et Biophysica Acta, 555:426–435 (1979).

*Primary Examiner*—Gollamudi S. Kishore
*Attorney, Agent, or Firm*—Arnold White & Durkee

[57] ABSTRACT

A method is disclosed for preparing a stable preliposomal powder which, when reconstituted with water or saline solution, forms a suspension of liposomes containing a polyene drug, such as nystatin. The method involves the steps of combining at least one phospholipid with a first organic solvent to form a first solution, adding a clarifying amount of water to the first solution, combining a polyene with a second organic solvent to form a second solution, combining the first and second solutions to produce a substantially clear combined solution, and then removing the organic solvents, leaving a powder.

4 Claims, No Drawings

LIPOSOMAL-POLYENE PRELIPOSOMAL POWDER AND METHOD FOR ITS PREPARATION

This application is a continuation of Ser. No. 08/204,642, filed on Mar. 1, 1994, now abandoned, which is a continuation of Ser. No. 07/902,891, filed Jun. 23, 1992, now abandoned, which is a continuation of Ser. No. 07/640,707, filed Jan. 14, 1991, now issued as U.S. Pat. No. 5,178,875, which is a continuation-in-part of Ser. No. 07/588,143, filed on Sept. 25, 1990, now abandoned, which is a divisional of Ser. No. 07/152,183, filed on Feb. 4, 1988, now abandoned, which is a continuation in part of Ser. No. 07/109,813, filed on Oct. 16, 1987, now issued as U.S. Pat. No. 4,950,432.

Background of the Invention

The present invention relates to a method of preparing a freeze-dried powder, which can be used to quickly and conveniently generate a liposomal formulation of a polyene such as nystatin.

Nystatin is a tetraene-diene polyene antibiotic, first isolated from *Streptomyces noursei*, which is used in the treatment of various fungal infections. Unfortunately, nystatin, as well as other polyenes, is not generally useful for parenteral administration, because of its high toxicity and insolubility in water. A formulation of a polyene, such as nystatin, which could be administered parenterally would substantially enhance the drug's therapeutic usefulness.

Some of the inventors of this patent previously discovered that these problems could be overcome by formulating nystatin in phospholipid vesicles, or liposomes. Such a liposomal formulation is considerably less toxic to the animal to which it is administered, but is still effective against fungal infection, and therefore is suitable for systemic use. U.S. Pat. No. 4,812,312 discloses that invention, and is incorporated here by reference.

One drawback to some liposomal drug formulations is their less-than-desirable shelf life. Another drawback is the relative complexity of the process needed to prepare them. In view of these drawbacks, it would be highly desirable to produce a stable, dry formulation which could be rehydrated when needed for treatment of a patient. Lyophilized, or freeze-dried, powders are a possible answer to this need. However, in order to be practical, a lyophilized powder must not only be stable and capable of reconstituting as liposomes, it must capable of being prepared by a process that is simple and inexpensive enough so that it will be practical and cost-effective for commercial use.

The present invention solves these and other problems found in the prior art.

SUMMARY OF THE INVENTION

The present invention generally concerns a method for producing a powder suitable for the preparation of polyene-containing liposomes upon suspension in an aqueous solution. In one aspect, the present invention relates to a method of preparing a liposomal-polyene preliposomal powder, comprising the steps of combining at least one phospholipid with a first organic solvent to form a first solution; combining the first solution with a clarifying amount of water, forming a clarified first solution; combining polyene with a second organic solvent to form a second solution; combining the clarified first solution and the second solution to produce a substantially clear combined solution; and removing substantially all the solvent from the combined solution. In a preferred embodiment of this aspect of the present invention, a method of preparing a liposomal-nystatin preliposomal powder comprises the steps of combining dimyristoyl phosphatidyl choline and dimyristoyl phosphatidyl glycerol with t-butyl alcohol to form a first solution; combining the first solution with a clarifying amount of water, forming a clarified first solution; combining nystatin with dimethyl sulfoxide to form a second solution; combining the clarified first solution and the second solution to produce a substantially clear combined solution; and removing substantially all the t-butyl alcohol and dimethyl sulfoxide from the combined solution.

In another aspect, the present invention relates to a method of preparing a parenterally-administrable polyene preparation, comprising the steps of combining at least one phospholipid with a first organic solvent to form a first solution; combining the first solution with a clarifying amount of water, forming a clarified first solution; combining polyene with a second organic solvent to form a second solution; combining the clarified first solution and the second solution to produce a substantially clear combined solution; removing substantially all the solvent from the combined solution, thereby forming a preliposomal powder; and adding a pharmaceutically acceptable solvent to the preliposomal powder.

In another aspect, the present invention relates to a liposomal-polyene preliposomal powder prepared by a method comprising the steps of combining at least one phospholipid with a first organic solvent to form a first solution; combining the first solution with a clarifying amount of water, forming a clarified first solution; combining polyene with a second organic solvent to form a second solution; combining the clarified first solution and the second solution to produce a substantially clear combined solution; and removing substantially all the solvent from the combined solution, leaving a preliposomal powder. A particular embodiment of this aspect of the present invention is a lyophilized nystatin powder, comprising nystatin, dimyristoyl phosphatidyl choline, and dimyristoyl phosphatidyl glycerol, where the weight ratio of DMPC to DMPG is about 7:3, and where the powder is free of halogenated solvents. It is believed that the relative proportions of water and the first organic solvent affect the nature and characteristics of the resulting powder, including the way in which the powder behaves when hydrated. The polarity of the solution, with the proportion of water preferably being no greater than the proportion of the first organic solvent, is believed to affect the organization of the materials in solution, and thus the nature of the powder that is ultimately formed.

In another aspect, the present invention relates to a substantially clear, filterable polyene solution, comprising at least one polyene, at least one phospholipid, at least one organic solvent, and a clarifying amount of water.

The present invention, in its various aspects, provides surprising advantages over the prior art. For example, it has been found that merely combining phospholipids with an organic solvent such as t-butyl alcohol produces a solution that is not clear, and therefore is not desirable for use in producing a preliposomal powder. The present invention makes use of the surprising discovery that a clarifying amount of water can be added to the solution of polyene and organic solvent, yielding a clear solution which is suitable for use in subsequent steps of the method. The clarity of solution permits substantially uniform contact between the polyene and the phospholipids in subsequent stages. Further, the filterability of this solution permits contaminating microorganisms to be removed readily prior to lyophilization. This latter point is particularly important with respect to polyenes such as nystatin, which would not tolerate autoclaving as an alternate means of removing microorganisms.

It is also surprising that the clarifying amount of water needed for use in the method of the present invention can range from about 10% of the amount of the first organic solvent (e.g., t-butyl alcohol) upward. It is known that in other alcohol-lipid solutions, such large amounts of water cannot be used without causing precipitation. For example, precipitation will result in a solution of egg phosphatidyl choline in ethanol when the amount of water added exceeds 30% of the volume of alcohol.

It is also surprising that a second organic solvent, such as dimethyl sulfoxide, can be added to the clear solution containing the clarifying amount of water in conjunction with the addition of polyene without causing either the lipids or the polyene to precipitate. Again, the surprising clarity of the final solution renders the solution more readily filterable, and thus makes the overall process more advantageous and economical. Without wishing to be bound by any particular theory to explain these surprising results, it is believed that the first organic solvent, such as t-butyl alcohol, forms a solvation complex with the phospholipids, a complex that arranges itself in a micellular configuration such that it remains clear even in a vast excess of water or solvent. It is also believed that the polyene arranges itself in a complex that may be micellular in nature, in the presence of the phospholipids.

The present invention facilitates the formulation and reconstitution of liposomal-polyene from a degradation-resistant preliposomal powder. The simplicity of the present invention makes it suitable for large-scale manufacturing. Further, it produces a stable powder which can be easily stored for at least one year. In addition, when reconstituted, the product of the present method forms multilamellar liposomes which have a mean size that is suitable for administration to humans, for example in the systemic administration of liposomal nystatin to treat a fungal or viral infection.

DESCRIPTION OF THE SPECIFIC EMBODIMENTS OF THE INVENTION

A method in accordance with the present invention can include the following steps. First, one or more phospholipids are combined with a first organic solvent. The phospholipids which can be used are those which are suitable for the preparation of liposomes, and are well-known to those skilled in the art. Two specific examples that are particularly preferred in the present invention are dimyristoyl phosphatidyl choline and dimyristoyl phosphatidyl glycerol. The preferred weight ratio of DMPC:DMPG is approximately 7:3. Suitable organic solvents for use as the first organic solvent include t-butyl alcohol. The ratio of phospholipid to first organic solvent is preferably between about 10 g:160 cc and about 10 g:640 cc, and is most preferably about 10 g:320 cc. The combination of phospholipid and first organic solvent creates a first solution.

A clarifying amount of water is then added to the first solution, resulting in the clarification of that solution. A "clarifying amount of water" is used in this patent to mean an amount of water that will be effective to clarify the already-existing solution of phospholipid and first organic solvent. This amount of water is preferably equal to at least 10% by weight of the amount of first organic solvent in the first solution. The clarifying amount of water can range up to 100% by weight of the amount of first organic solvent, and can go even higher. In a preferred embodiment, the volume ratio of water to t-butyl alcohol is about 1:4. In other words, in a preferred embodiment, the ratio of phospholipid to t-butyl alcohol to water is 10 g:320 cc:80 cc.

The next step is to combine at least one polyene with a second organic solvent to form a second solution. The ratio of polyene to second organic solvent preferably ranges from about 1 g:5 cc to about 1 g:25 cc. Suitable polyenes include nystatin, amphotericin B, filipin, hamycin, and mepartricin. Nystatin is particularly preferred. Suitable second organic solvents include dimethyl sulfoxide (DMSO) and dimethyl formamide. In one preferred embodiment of the present invention, the ratio of nystatin to DMSO is approximately 1 g:7 cc.

The first and second solutions can be filtered separately before they are combined, for example through a 0.45 AM pore size filter cartridge. However, any contaminants which are present, such as microorganisms, can usually be removed in a single filtration step immediately before the organic solvents are removed from the combined solution. If the amount of contaminants present in the combined solution causes problems with filtration, then additional filtration steps can suitably be added.

The clarified first solution is then combined with the second solution to produce a substantially clear combined solution. Preferably, the concentration of nystatin in the combined solution is about 2.5–2.75 mg/ml and the concentration of phospholipid is about 25–27.5 mg/ml. The ratio of solids to liquid in this solution is believed to be important to the ready reconstitution of the preliposomal powder into liposomes when water is added. If the solids concentration is too high, the resultant dry product is denser than optimal and does not perform as well as desired on reconstitution.

Next, substantially all of the organic solvents are removed from the combined solution, for example by lyophilization, producing a preliposomal powder. The powder can be reconstituted into an aqueous formulation of liposomal polyene by adding a pharmaceutically acceptable solvent, such as water or saline solution.

The following is a specific example of how the process of the present invention can be performed. The quantities given below are for the sake of example, and could be scaled up proportionately.

Seven g of dimyristoyl phosphatidyl choline and 3 g of dimyristoyl phosphatidyl glycerol (Lipoid KG, Ludwigshafen, Germany) are transferred to a first mixing vessel. To this vessel, 250 cc of t-butyl alcohol are added, and the solution is mixed. This first solution is cloudy at this point. Then, 250 cc of water are added and mixed until dissolved, resulting in a clarified solution. Nystatin (1.1 g, American Cyanamid, Pearl River, N.Y.) is separately transferred to a second mixing vessel, and 7 cc of dimethyl sulfoxide is added. The theoretical amount of nystatin needed for this particular preparation is 1 g (1:10 weight ratio of nystatin: phospholipid), but it is preferred to add 110% of the theoretically needed amount. This second solution is mixed until dissolved, and is mixed with the first solution to produce a combined solution, which is clear yellow.

The combined solution is analyzed for nystatin concentration by a spectrophotometric assay. If needed to correct the concentration, an appropriate volume of a diluent, such as water, is added.

Next, the combined solution is passed through a sterile, 0.22 $\mu$M pore size membrane, and 20 cc of the filtrate is transferred into a 100 cc vial. A lyophilization stopper is then loosely placed on the filled vial, and the vial is placed into a sterile lyophilization chamber, where the solvents are removed. While the vial is placed into the chamber, a thermocouple probe is inserted into the vial, in order to be able to monitor its temperature during the freeze-drying process. When a plurality of vials are placed in the chamber, thermocouples are placed so that a reasonable cross-section of the chamber is monitored (e.g., top, middle, and bottom of chamber).

The circulating fluid in the freeze-drying chamber is adjusted to −45° C. The chamber is then evacuated to a vacuum of no more than 200 microns. The circulating fluid temperature is then ramped to 10° C. over a minimum of about 24 hours at an approximate rate of 2.3° C./hour. The chamber vacuum is adjusted to sweep slowly from 60 to 100 microns using N to control the sweep rate. When the coldest thermocouple reaches −5° C., the circulating fluid is ramped to 28° C. over a minimum of four hours at an approximate rate of 5.5° C./hour. When the coldest thermocouple reaches 28° C., the product is at terminal drying temperature, and is held there for about 12–30 hours. At the end of this time, the chamber is adjusted to atmospheric pressure using N and NF passed through a microbiologically retentive filter. Prior to unloading the freeze-drying chamber, the temperature of the circulating fluid is adjusted to 25° C. At the end of the lyophilization cycle, the vials are filled with nitrogen gas and the stoppers are fully closed. The lyophilized powder appears pale yellow, and contains less than 2% residual t-butyl alcohol and less than 1% residual dimethyl sulfoxide.

The formulation is reconstituted by adding about 50 cc of water to the powder for every 1 g of polyene. It is preferred to heat the solution above 27° C., most preferably between about 30° and 45° C. for about 15–60 minutes, to aid the hydration process. The powder initially disperses into clumps several tens of $\mu$ in diameter. When the solution is warmed, the clumps hydrate and spontaneously form liposomes. The temperature at which this transition occurs may be due to the phase transition temperature of the lipids, which for the above-described materials is around 23° C.

After reconstitution, the mean particle size is about 2–3 $\mu$M, with not more than 1% having a diameter over 8 $\mu$M. The incorporation efficiency of drug in liposomes is greater than 90%, and may approach 100%.

The preceding description is intended to illustrate the present invention. It is not intended to be an exhaustive list of all possible embodiments of the invention. Persons skilled in this field will recognize that modifications could be made to the description given above that would remain within the scope of the invention.

We claim:

1. A lyophilized preliposomal nystatin powder, comprising the polyene nystatin, the phospholipid dimyristoyl phosphatidyl choline, and the phospholipid dimyristoyl phosphatidyl glycerol, where the ratio of dimyristoyl phosphatidyl choline to dimyristoyl phosphatidyl glycerol is about 7:3, and where the powder is free of halogenated solvents.

2. The powder of claim 1 made by the method comprising the steps of:
   a. combining at least one phospholipid with a first organic solvent to form a first solution;
   b. combining the first solution with a clarifying amount of water, forming a clarified first solution;
   c. combining polyene with a second organic solvent to form a second solution;
   d. combining the clarified first solution and the second solution to produce a substantially clear combined solution; and
   e. removing substantially all the solvent from the combined solution by initial freeze-drying at about −45° C. at a vacuum of no more than 200 microns Hg and increasing said temperature by approximately 2.3° C./hour to 10° C.

3. A liposomal-polyene preliposomal powder prepared by a method comprising the steps of:
   a. combining at least one phospholipid with a first halogen free organic solvent to form a first solution;
   b. combining the first solution with a clarifying amount of water, forming a clarified first solution;
   c. combining polyene with a second halogen free organic solvent to form a second solution;
   d. combining the clarified first solution and the second solution to produce a substantially clear combined solution; and
   e. removing substantially all the solvent from the combined solution by initial freeze-drying at about −45° C. at a vacuum of no more than 200 microns Hg and increasing said temperature by approximately 2.3° C./hour to 10° C.

4. A method of preparing a halogen-free reconstituted polyene-liposomal solution having a mean particle size of 2–3 $\mu$m, with not more than 1% of the liposomes having a diameter over 8 $\mu$m by the process of
   (i) preparing a liposomal-polyene preliposomal powder prepared by a method comprising the steps of:
      a. combining at least one phospholipid with a first halogen free organic solvent to form a first solution;
      b. combining the first solution with a clarifying amount of water, forming a clarified first solution;
      c. combining polyene with a second halogen free organic solvent to form a second solution;
      d. combining the clarified first solution and the second solution to produce a substantially clear combined solution; and
      e. removing substantially all the solvent from the combined solution by initial freeze-drying at about −45° C. at a vacuum of no more than 200 microns Hg and increasing said temperature by approximately 2.3° C./hour to 10° C; and
   (ii) adding a pharmaceutically acceptable solvent to the preliposomal powder.

* * * * *